US010564128B2

(12) United States Patent
Chinta (10) Patent No.: US 10,564,128 B2
(45) Date of Patent: *Feb. 18, 2020

(54) METHOD AND DEVICE FOR THE NEAR SURFACE, NONDESTRUCTIVE INSPECTION BY MEANS OF ULTRASOUND OF A ROTATIONALLY SYMMETRIC WORKPIECE HAVING A DIAMETER THAT CHANGES FROM SECTION TO SECTION

(71) Applicant: GE Sensing & Inspection Technologies GmbH, Hurth (DE)

(72) Inventor: Prashanth Kumar Chinta, Huerth (DE)

(73) Assignee: GE Sensing & Inspection Technologies GmbH, Hurth (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/157,987

(22) Filed: Oct. 11, 2018

(65) Prior Publication Data
US 2019/0107515 A1    Apr. 11, 2019

Related U.S. Application Data (63) Continuation of application No. 14/651,575, filed as application No. PCT/EP2013/071287 on Oct. 11, 2013, now Pat. No. 10,139,373.

(30) Foreign Application Priority Data

Dec. 11, 2012   (DE) .................. 10 2012 112 120

(51) Int. Cl.
*G01N 29/04*   (2006.01)
*G01N 29/06*   (2006.01)
(Continued)

(52) U.S. Cl.
CPC ......... *G01N 29/043* (2013.01); *G01N 29/069* (2013.01); *G01N 29/0645* (2013.01);
(Continued)

(58) Field of Classification Search
CPC ............. G01N 29/043; G01N 19/0645; G01N 29/069; G01N 29/221; G01N 29/38
See application file for complete search history.

(56) References Cited

U.S. PATENT DOCUMENTS 3,572,087 A   3/1971 Parks
4,537,073 A   8/1985 Ooshiro
(Continued)

FOREIGN PATENT DOCUMENTS

GB   2285129 A   6/1995

OTHER PUBLICATIONS

The International Search Report and Written Opinion issued in connection with WO Patent Application No. PCT/EP2013/071287 dated Jan. 10, 2014.
(Continued)

*Primary Examiner* — Helen C Kwok
(74) *Attorney, Agent, or Firm* — Mintz Levin Cohn Ferris Glovsky and Popeo, P.C.

(57) ABSTRACT

A method and a device for the near-surface, non-destructive inspection by means of ultrasound of a rotationally symmetric workpiece having a diameter that changes from section to section are provided. The method and device are based on the insonification of an ultrasonic test pulse into the workpiece at a defined insonification angle and the subsequent recording of an ultrasonic echo signal from the workpiece. Echo signals that trace back to a near-surface region ROI of the workpiece are identified and evaluated. Then, a graphic representation of the surface of the workpiece is generated.

22 Claims, 3 Drawing Sheets

(51) Int. Cl.
    *G01N 29/22*          (2006.01)
    *G01N 29/38*          (2006.01)

(52) U.S. Cl.
    CPC ........... *G01N 29/221* (2013.01); *G01N 29/38* (2013.01); *G01N 2291/0289* (2013.01); *G01N 2291/044* (2013.01); *G01N 2291/056* (2013.01); *G01N 2291/2634* (2013.01)

(56) References Cited

U.S. PATENT DOCUMENTS

| | | |
|---|---|---|
| 4,574,637 A | 3/1986 | Adler |
| 5,804,727 A | 9/1998 | Lu |
| 5,992,236 A | 11/1999 | White |
| 10,139,373 B2 * | 11/2018 | Chinta ................. G01N 29/043 |
| 2003/0089171 A1 | 5/2003 | Kenefick et al. |
| 2004/0118210 A1 * | 6/2004 | Tooma ..................... B06B 1/06 |
| | | 73/625 |
| 2005/0183505 A1 | 8/2005 | Kono |
| 2006/0130587 A1 | 6/2006 | Howard |
| 2006/0201252 A1 | 9/2006 | Georgeson |
| 2007/0084288 A1 | 4/2007 | Thomas |
| 2008/0006091 A1 | 1/2008 | McKeon |
| 2008/0041160 A1 | 2/2008 | Wright |
| 2008/0121040 A1 | 5/2008 | MacLauchlan |
| 2009/0320599 A1 * | 12/2009 | Burat ................... G01N 29/043 |
| | | 73/622 |
| 2010/0031751 A1 | 2/2010 | Perkins et al. |
| 2010/0170344 A1 | 7/2010 | Lesage |
| 2011/0083512 A1 | 4/2011 | Imbert |
| 2012/0060611 A1 | 3/2012 | Thommen-Stamenkov et al. |
| 2012/0191377 A1 | 7/2012 | Engl et al. |
| 2015/0330948 A1 | 11/2015 | Lingenberg |

OTHER PUBLICATIONS

German Search Report issued in connection with related Application No. 102012112121.4 dated Sep. 2, 2013.

Erhard et al., "Ultrasonic Phased Array System for Railroad Axle Examination", AIAA(90-2421) Experimental Turbofan Using Liquid Hydrogen and Liquid Natural Gas as Fuel, In: NDT.net, vol. 8, No. 3, pp. 1-6, Mar. 2003.

* cited by examiner

METHOD AND DEVICE FOR THE NEAR SURFACE, NONDESTRUCTIVE INSPECTION BY MEANS OF ULTRASOUND OF A ROTATIONALLY SYMMETRIC WORKPIECE HAVING A DIAMETER THAT CHANGES FROM SECTION TO SECTION

CROSS REFERENCE TO RELATED APPLICATIONS

This application is a continuation of U.S. patent application Ser. No. 14/651,575, entitled "METHOD AND DEVICE FOR THE NEAR SURFACE, NONDESTRUCTIVE INSPECTION BY MEANS OF ULTRASOUND OF A ROTATIONALLY SYMMETRIC WORKPIECE HAVING A DIAMETER THAT CHANGES FROM SECTION TO SECTION," filed on Jun. 11, 2015, which is a national stage application, filed under 35 U.S.C. § 371, of International Application No. PCT/EP2013/071287, filed on Oct. 11, 2013, and claims the benefit of, and priority to, DE Patent Application No. 102012112120.6, filed on Dec. 11, 2012, each of which is incorporated by reference herein in its entirety.

BACKGROUND

The subject matter of the present invention is a method and device for the near-surface, non-destructive inspection by means of ultrasound of a rotationally symmetric workpiece having a diameter that changes from section to section. In this case, the workpiece does not have an internal cut-out. The method and the device are suited, in particular, for the inspection of a workpiece with an anisotropic sound velocity. For example, an anisotropic sound velocity is frequently observed, for example, in forged solid shafts which can be used, for instance, in rail vehicles.

Wheel sets of rail vehicles generally include one pair of wheels mounted on a rigid solid or hollow shaft. The shafts used in this case often have external diameters changing from section to section, for example defined regions for the accommodation of functional components, such as the wheels, anti-friction bearings or brake disks. It is obvious that the shafts of wheel sets of rail vehicles constitute safety-relevant components that are subject to natural wear over the long life span of rail vehicles. For this reason, their freedom from flaws has to be determined by means of non-destructive inspection methods not only during the production of wheel sets for rail vehicle. Rather, a regular inspection with regard to freedom from flaws of all components, in this case particularly the wheels as well as the shaft used, is required also over the entire life span of a wheel set. In practices, the most frequent wear phenomenon observed in shafts of wheel sets of rail vehicles is the occurrence of incipient cracks, i.e. crack-like fatigue failures that start at the surface of the respective shaft. Every rail vehicle operator there-fore has to provide suitable inspection methods and devices in order to check the wheel sets of rail vehicles with regard to their freedom from flaws regularly.

Until this day, the inspection by means of ultrasound of rotationally symmetric workpieces having diameters that change from section to section, in particular of solid shafts of rail vehicles, constitutes a particularly challenging inspection task. On the one hand, this is due to the fact that, as a rule, rotationally symmetric workpieces with a diameter that changes from section to section only have few surfaces suitable for coupling in ultrasound. Furthermore, such workpieces are often forgings. As a rule, they have an increased anisotropy of the sound velocity for ultrasound.

Moreover, the inspection of a wheel set of a rail vehicle often entails a downtime 5 of the rail vehicle, which is directly connected to high downtime costs due to the rail vehicle being out of service. In order to minimize them, it would be desirable to be able to inspect a fully assembled wheel set, i.e. a wheel set with assembled bearings and/or brake disks. If they are mounted, then an insonification from the shaft or from the end face (e.g. by means of a conical probe) is not possible with the inspection methods known from the prior art.

Finally, the generation of an easily interpreted representation of the results of an ultrasound inspection obtained on a rotationally symmetric workpiece constitutes a problem which, as far as the applicant is aware, is so far unsolved.

SUMMARY OF INVENTION

It is therefore the object of the present invention to propose a method and device for the near-surface, non-destructive inspection by means of ultrasound of a rotationally symmetric workpiece having a diameter that changes from section to section, wherein the workpiece has no internal cut-out. In this case, the results of the ultrasonic inspection are supposed to be particularly easily interpretable.

This object is accomplished by a method and a device according to embodiments of the present invention. The dependent claims dependent claims can be freely combined with each other in any way within the context of what is technically feasible. However, such a combination is not an absolute requirement.

The method according to an embodiment of the invention serves for the near-surface, nondestructive inspection by means of ultrasound of a rotationally symmetric workpiece having a diameter that changes from section to section. In this case, the workpiece has no rotationally symmetric internal cut-out. To make matters simple, such a workpiece will be referred to below as "solid shaft". In its simplest form, the method comprises the following process steps:

a. insonifying an ultrasonic test pulse into the workpiece at a coupling location E at a defined insonification angle Theta, b. recording an ultrasonic echo signal from the workpiece, in an embodiment, at the insonification angle Theta, c. selecting a travel time interval I depending on the sound path W of the ultrasonic test pulse in the workpiece, the selected travel time interval I corresponding to a preselected near-surface region ROI (ROI: "region of interest") of the workpiece, d. generating an echo value G by analyzing the ultrasonic echo signal in the selected travel time interval I, and e. generating a representation of the surface of the workpiece, wherein the echo value G is depicted in the representation in a spatially resolved manner.

Generally, the sound path W of the ultrasonic test pulse in the workpiece is dependent on the workpiece geometry, the coupling location E, the insonification angle Theta, the insonification direction Phi (see below) and on the acoustic properties both of the workpiece as well as of the ultrasonic test probe used for the generation of the ultrasonic test pulse.

The method according to the invention provides an inspection method which permits displaying the result of an ultrasonic inspection of a rotationally symmetric workpiece with regard to near-surface defects in a manner that is particularly intelligible to an examiner. In this case, the representation of the workpiece surface generated according to the invention is two-dimensional, e.g. in the form of a C image, or it is spatial, with the spatial, i.e. three-dimensional representation being used in an embodiment. It is obvious to a person skilled in the art that the generation of a graphic representation of the workpiece described herein comprises both the generation of a data set representing a representation of the workpiece, for example in the sense of a CAD model, as well as the actual depiction of a graphic representation of the workpiece on a suitable depicting unit, e.g. on a suitable display, which can be connected, for example, to a device according to the invention.

In an embodiment of the method, a point w on the surface of the representation of the workpiece is assigned to the sound path W of an ultrasonic test pulse in the workpiece. For example, the location of the first incidence of the ultrasonic test pulse on the internal workpiece surface can in this case be used for the point w. In the graphic representation of the workpiece surface, the echo value G of the ultrasonic test pulse assigned to this point w is then presented in a suitable manner, e.g. by a local color or brightness coding. This is described in more detail below by way of example within the context of the exemplary embodiment.

If the largest amplitude of the ultrasonic echo signal occurring in the selected travel time interval I is used as the echo value G, than an embodiment of the inspection method according to the invention is obtained because it can be easily technically implemented.

In another development of the method according to an embodiment of the invention, the ultrasonic echo signal is subjected, at least in the selected travel time interval I, to a travel time-dependent or/and insonification angle-dependent amplification. In this way, sound-attenuating effects, for example due to the geometric expansion of the sound field along the propagation direction, its attenuation in the workpiece, for example due to scattering on anisotropies, as well as a possible angular dependence of the reflection of the ultrasonic test pulse on an internal boundary surface of the workpiece, can be compensated. Consequently, flaws of the same size and orientation generate echo signals of approximately the same size, irrespective of their position in the workpiece, which in turn improves even further the interpretability of the result of the test method.

It is obvious to the person skilled in the art that the recorded ultrasonic echo signal can be subjected to a suitable signal conditioning process, e.g. for improving the signal-to-noise ratio, particularly after a digitization process. For this purpose, a variety of methods are known in prior art.

The signal-to-noise ratio can also be significantly improved if the method steps a to d. are executed several times for a fixed coupling location E and a fixed insonification angle Theta and if a mean value <G> of the generated echo values G is formed. In step e., this mean value <G> is then shown in the representation in a spatially resolved way.

In a development of the method according to an embodiment of the invention, a plurality of successive ultrasonic pulses is insonified into the workpiece at different insonification angles Theta. It is possible to vary the insonification angle Theta from pulse to pulse; however, it is also possible to vary, only after a finite series of pulses at the same insonification angle, the insonification angle for a subsequent pulse series. Thus, a mean value formation of the flaw signals to be evaluated, over a plurality of echo signals resulting from a plurality of ultrasonic test pulses coupled in at the same insonification angle Theta, improves the signal-to-noise ratio. In the process, the method according to an embodiment of the invention is carried out for each ultrasonic test pulse insonified into the workpiece. In another embodiment of the method, the position of the coupling location E on the workpiece surface relative to its axis of symmetry S is kept substantially constant in the process. "Kept substantially constant" in this context means, in particular, that the position X of an ultrasonic test probe comprising an ultrasonic transducer for generating the ultrasonic test pulses is kept constant relative to the axis of symmetry S of the workpiece. In the case of the ultrasonic test probes for oblique insonification with a variable insonification angle commonly used in practice, in which the ultrasonic transducer is disposed, for example, on a wedge-shaped leading body, the actual coupling location changes slightly if the insonification angle is changed. This effect is to be allowed to be neglected in this case.

So-called "phased array" ultrasonic test probes, which are known in the prior art and whose application in the context of the present invention will be discussed in more detail, permit an electronic tuning of the insonification angle Theta over a broad angle range. Particularly in connection with the embodiments of the method according to an embodiment of the invention, in which the insonification angle Theta is varied between different ultrasonic test pulses of a test pulse series, the use of such "phased array" test probes with an electronically tunable insonification angle Theta has proven to be particularly advantageous. Particular advantages are obtained if, furthermore, test probes in accordance with the teaching of the family of PCT/EP2010/0566154 are being used, with this teaching being added to the disclosure of the present application by this reference. The use of such test probes allows taking into account the curvature of the coupling surface in the 35 axial and radial directions, which is advantageous in particular in the case of shafts of wheel sets whose shaft geometries can in part also be curved completely in the longitudinal direction, so that at least with components such as wheels, bearings or brake disks mounted on the shaft—there is no purely cylindrical region with a constant diameter for ultrasonic coupling.

In an embodiment, the insonification of the one or more ultrasonic test pulses into the workpiece is carried out in such a way that the sound path W of the ultrasonic test pulse(s) in the workpiece and the axis of symmetry S of the rotationally symmetric workpiece span a common plane, i.e. that the sound path W of the ultrasonic test pulse(s) intersects the axis of symmetry S of the rotationally symmetric workpiece. This common plane is hereinafter also referred to as insonification plane P. The preselected near-surface region ROI as a rule is located behind this point of intersection.

In another development of the method according to an embodiment of the invention, the relative position of the test probe position X and the workpiece is not altered while a first part of the process of the inspection method is carried out, in which the insonification angle Theta is changed continuously. This means that the above-mentioned condition is satisfied in this first part of the process for all ultrasonic test pulses coupled into the workpiece.

Since this is a rotationally symmetric workpiece, an effective transsonification of the workpiece can be realized, in particular, by a relative rotation of the workpiece and the ultrasonic test probe about the axis of symmetry of the workpiece, characterized by a rotation angle Beta. Therefore, in another development of the method according to an embodiment of the invention, a relative rotary movement of the test probe and the workpiece of the above-mentioned type is realized in a second process step, with the rotation angle Beta being at least 360° according to an embodiment. In an embodiment, the above-mentioned condition is adhered to in the process, according to which the sound path W of every ultrasonic test pulse coupled into the workpiece intersects the axis of symmetry S of the workpiece. The simplest way to realize a relative rotary movement of the test probe and the workpiece about the axis of symmetry S of the workpiece is by rotating the workpiece about its axis of rotation S under the test probe, which is held fixed in its position X.

In an embodiment of the method, while maintaining the position of the ultrasonic test probe relative to the axis of symmetry S of the workpiece, a series of ultrasonic test pulses is insonified into the workpiece, while the insonification angle Theta and the rotation angle Beta is varied at the same time. In this case, having gone through a predetermined interval for the insonification angle Theta, for example, a gradual relative rotary movement of the ultrasonic test probe and the workpiece is carried out about the axis of symmetry S of the workpiece. Thus, an electronic tuning of the insonification angle Theta is possible over an angle range of at least 30° to 60°, or of at least 20° to 75°. Subsequently, a relative rotary movement of the test probe and the workpiece about the axis of symmetry S of the workpiece by, for example, maximally 5°, particularly maximally 1°, and more particularly maximally 0.5°, is carried out. For this new relative position of the test probe and the workpiece, a series of ultrasonic test pulses is then insonified into the workpiece at a varying insonification angle Theta. Then, another relative rotation of the test probe and the workpiece takes place, etc. On the whole, the relative rotation angle Beta of the test probe and the workpiece about the axis of symmetry S of the workpiece over a complete test cycle is to be at least 360°, in an embodiment, it is 360° or an integral multiple of 360°.

In an alternative development of the method according to an embodiment of the invention, the insonification angle Theta and the relative rotation angle Beta of the workpiece and the ultrasonic test probe about the axis of symmetry S of the workpiece are varied simultaneously, with the rotating speed of, for example, the workpiece about its own axis of symmetry S being selected to be so low that the result is still a sufficient geometric overlap of the ultrasonic test pulses in the ROI in the workpiece.

In another development of the method according to an embodiment of the invention, two groups of ultrasonic test pulses are insonified into the workpiece. In this case, the first group of ultrasonic test pulses has a travel direction which has one component in the positive direction of the axis of symmetry S of the workpiece. In contrast, the second group of ultrasonic test pulses has a travel direction which has one component in the negative direction of the axis of symmetry S of the workpiece. In an embodiment, the first and the second groups of ultrasonic test pulses are coupled into the workpiece at substantially the same location. For this purpose, it is possible, in particular, to integrate two ultrasonic transducers into a single test probe that transmit the first and second groups of ultrasonic test pulses. By means of this development of the method according to an embodiment of the invention it is possible to virtually double the tunable angle range, and thus 5 the sector of the workpiece to be acquired from a test probe position X (relative to the axis of symmetry S of the workpiece), which makes it possible to carry out the method with an efficiency that is increased even more.

In an embodiment, the inspection method is repeatedly carried out for different test probe positions X on the workpiece surface. This third part of the process serves for acquiring as large a (near-surface) volume of the workpiece as possible. As a rule, carrying out the method at a few discrete test probe positions X is sufficient for acquiring the entire (near-surface) volume of the workpiece, even in the case of ragged workpiece geometries.

If all of the three parts of the process are run through for a workpiece, then, for most workpiece geometries, the entire near-surface volume of the workpiece can be transsonified with the ultrasonic test pulses and thus inspected. The representation of the workpiece surface generated therefrom according to the invention thus contains complete information on the result of the ultrasound inspection of the entire near-surface volume of the workpiece. Particularly informative is the graphic representation described herein of the result of the ultrasonic inspection method according to the invention, because a complete relative rotation of the test probe and the workpiece by 360° or an integral multiple thereof about the axis of symmetry of the workpiece has taken place during the inspection of the workpiece. Because the method is furthermore carried out starting from different test probe positions X, the entire volume of the near-surface region of the workpiece is transsonified and subsequently graphically represented provided the rotationally symmetric workpiece has a suitable geometry.

A development of the method according to an embodiment of the invention permits the reduction of the process duration by effectively reducing the amount of data to be analyzed. This is possible by limiting the evaluation of the recorded ultrasonic echo signals, which correspond to, in part, very long travel distances of the test pulse in the workpiece that occur primarily at large insonification angles Theta, to those echo signals that result from a preselected near-surface region of the workpiece to be inspected. Within the context of the present invention, this preselected region is also referred to as ROI (="region of interest"). As a rule, the ROI to be used during the execution of the method is determined by the examiner with knowledge of the material properties as well as of the geometry of the workpiece. As a rule, in an embodiment, the ROI is selected to be adjacent to that internal workpiece surface at which a first reflection of the ultrasonic test pulse in the workpiece occurs.

The ROI can be limited, for example, to the sector of the workpiece that extends radially inwardly, from the workpiece surface, by a few to a few tens of millimeters, for example by 30 to 60 millimeters, or by 40 millimeters.

Also, the ROI can be defined differently from section to section along the axis of symmetry of the workpiece, e.g. in regions with a changing shaft diameter, it can have a larger extent than in regions with a constant diameter.

Thus, ROI can also be deliberately selected to be larger in some sections, e.g. in order to depict displays from a wheel, bearing or brake seat possibly formed on the solid shaft.

Because of the existing uncertainty with regard to the sound velocity in a forged workpiece, it is advantageous to limit the ROI not only up to the incidence of the ultrasonic test pulse on the internal workpiece surface, but a certain travel time beyond, i.e. an internal total reflection on the workpiece surface may possibly occur in the ROI. However, the ultrasound testing pulse at least reaches the internal workpiece surface with a very good degree of certainty.

The travel time interval to be selected that corresponds to the ROI relates to the response time between the ultrasonic test pulse being coupled into the workpiece and the arrival of ultrasonic echo signals. The workpiece geometry is presumed to be known, as are the acoustic properties of the workpiece. Moreover, the coupling location E of the ultrasonic pulse, the insonification angle Theta and the insonification direction are known. For example, the insonification direction can be defined via the inclination angle phi of the sound propagation direction with respect to the plane defined by the axis of symmetry S and the coupling location E. In embodiments of the method according to the invention, the inclination angle phi is zero, i.e. the sound path W and the axis of symmetry S of the workpiece span a common plane P. The coupling location E is directly linked to the test probe position X on the workpiece surface and the insonification angle Theta. The sound path W of the ultrasonic test pulse in the workpiece can be determined from this, which, when a workpiece geometry and workpiece properties are given, is generally a function of the test probe position X, of the insonification angle Theta and of the inclination angle phi. In particular, the travel time tROI_EIN can be determined after which the ultrasonic test pulse enters the ROI previously determined by the examiner. Furthermore, a travel time tROI_AUS can be determined after which the first reflection of the ultrasonic test pulse on an internal workpiece surface has occurred. For a given insonification angle Theta, the ROI can be defined via this travel time interval I, i.e. every echo signal recorded after a response time tAntwort with 2tROI_EIN≤tAntwort≤2tROI_AUS results from an ultrasound reflector (e.g. a local anisotropy in the material structure of the workpiece, the local workpiece geometry, a flaw) in the ROI. It is obvious that the travel time interval I is, as a rule, dependent on the given insonification angle Theta.

In a development, the ROI is defined via the travel time interval I selected (and thus to be analyzed) for a given insonification angle Theta. The basis is the sound velocity for the ultrasonic test pulse in the workpiece, which can be specified only with a certain uncertainty. The start of the travel time interval I is defined by the time 2tROI_EIN at which the ultrasonic test pulse hits the internal surface for the first time at the earliest, i.e. the highest possible sound velocity is used as a basis. The end of the travel time interval I is defined by the time 2tROI_AUS at which the ultrasonic test pulse hits the internal surface for the first time at the latest, i.e. the lowest possible sound velocity is used as a basis. It is thus ensured that the ultrasonic test pulse hits the internal workpiece surface in the selected travel time interval with certainty, i.e. the internal surface lies within the ROI in every case.

Optionally, the travel time interval I to be analyzed, and thus the ROI, can be additionally enlarged by a defined "allowance" (e.g. ±5%, ±10%, ±15%) added to the maximum or minimum sound velocity to be presumed. This constitutes an advantageous development of the above-mentioned embodiment. It can thus be accomplished that a near-surface region with a defined, in particular constant, thickness of, for example 30 to 60 mm, or 40 mm and above, is always being examined.

According to the development of the method according to an embodiment of the invention, the analysis with regard to flaw signals Fi of the ultrasonic echo signal recorded from the workpiece at the angle Theta is limited to the selected travel time interval I which corresponds to the near-surface region of the workpiece to be inspected.

In its development, an embodiment of the invention provides a practical method for an effective data reduction to an ROI to be individually defined by the user for the respective inspection task. This effective data reduction permits the use of very high pulse repetition rates in the range of up to a few kHz and a highest temporal resolution in the analysis of the ultrasonic echo signals. Moreover, near-surface flaws in the workpiece can be reliably detected by means of the method and the device, even in the case of a ragged workpiece geometry and further components possibly mounted on the workpiece surface, wherein the method and the device can be applied so effectively that excessively long inspection times are avoided.

In an alternative approach, which is also to be comprised by the invention, the echo signal recorded in a time-resolved manner is digitized substantially over a travel time interval I from the entry into the workpiece to the double travel time until the first incidence upon the internal workpiece surface on the side opposite from the test probe, whereby a comprehensive raw data set is generated. This is reduced to a subset of data points to be analyzed by selecting only those data points whose origins lie in the previously defined ROI. With regard to their result, both approaches lead to the selection of the same subset of data points/echo signals to be analyzed. With regard to their results, they are therefore to be considered as equivalent.

A device according to the invention serves for the near-surface, non-destructive inspection by means of ultrasound of a rotationally symmetric workpiece having a diameter that changes from section to section, wherein the workpiece has no rotationally symmetric internal cut-out. In particular, it is suitable for inspecting forged solid shafts of wheel sets of rail vehicles. A device according to the invention comprises at least the following features:

a) a test probe (40) for insonifying an ultrasonic test pulse into the workpiece (1) at a defined insonification angle Theta and for recording an ultrasonic echo signal from the workpiece (1), b) a control unit (20) configured to:

control the test probe (40) for insonifying an ultrasonic test pulse into the workpiece (1) at a defined insonification angle Theta, ii. record by means of the test probe (40) an ultrasonic echo signal from the workpiece (1), and, in an embodiment, at the angle Theta, iii. select a travel time interval I depending on the sound path W of the ultrasonic test pulse in the workpiece (1), with the selected travel time interval I corresponding to a near-surface region ROI of the workpiece (1), and iv. generate, by analyzing the recorded ultrasonic echo signal in the selected travel time interval I, an echo value G, and v. generate a representation (50) of the surface of the workpiece (1), wherein the echo value G is depicted in the representation (50) in a spatially resolved manner.

In particular, a device according to the invention is suitable for carrying out the method according to the invention. In developments of the device, the above-described embodiments of the method according to the invention are implemented in the control unit.

Therefore, these different embodiments in particular permit the realization of those advantages that were already discussed in connection with the method according to the invention, to which reference is made here.

In another development, the testing device comprises a guiding device configured to orient the test probe relative to the axis of symmetry S of the workpiece in such a way that the sound path W of the ultrasonic test pulse in the workpiece and the axis of symmetry S span a common plane, the insonification plane P. This means that the travel direction of the ultrasonic test pulses insonified by the test probe into the workpiece has one component in the direction of the axis of symmetry of the workpiece. By ensuring the above-described travel direction of the ultrasonic test pulses insonified into the workpiece using the guiding device, a particularly simple sound field results in the workpiece. This simplifies the subsequent signal processing and evaluation.

In a development of the testing device according to an embodiment of the invention, the test probe comprises an ultrasonic transducer divided into a plurality of individually controllable transducer segments. Such test probes are known from the prior art; they are referred to as "phased array" test probes and, for example, permit the electronic control of the insonification angle of the ultrasonic pulses generated by the ultrasonic test probe into the workpiece, given a suitable electronic control of the individual transducer segments. Ultrasonic test probes according to the teaching of the family of PCT/EP2010/056614 are used with particular preference. In an embodiment, the control unit is furthermore configured to control a test probe of the phased array type in the aforementioned manner so that the insonification angle Theta into the workpiece can be set electronically. Moreover, the control unit is configured to insonify by means of the test probe a series of ultrasonic test pulses into the workpiece at different insonification angles Theta.

In another development of the testing device according to an embodiment of the invention, the latter moreover comprises a rotating device. The rotating device is configured to generate a relative movement of the test probe and the workpiece, in such a way that the workpiece is rotated about its axis of symmetry S under the test probe. In an embodiment, the rotating device comprises a means for acquiring the rotation angle Beta of the relative movement, e.g. an encoder. Moreover, in an embodiment, it is connected to the control unit of the testing device in such a way that the acquired rotation angle Beta of the rotary movement can be transmitted to the control unit. In a simplified embodiment of this device, it is not the angle of the relative movement of the test probe and the workpiece that is actually applied by the rotating device which is acquired and transmitted by the rotating device to the control unit. Rather, the control unit is configured for controlling the rotating device in such a way that the latter generates a relative movement of the test probe and the workpiece about a rotation angle Beta predetermined by the control unit. An acquisition of the angle of the rotary movement that is actually executed does not have to be carried out in this case, i.e. an encoder, for example, can be omitted.

In another development of the testing device according to an embodiment of the invention, the test probe of the testing device comprises two ultrasonic transducers. They are characterized in that the travel direction of a first part of the pulses has one component in the direction of the axis of symmetry S of the workpiece and the travel direction of a second part of the pulses has one component oriented contrary to the direction of the axis of symmetry S. A particularly compact construction is provided if the two ultrasonic transducers are mounted on a common leading body, which may, for example, consist of polystyrene, polycarbonate or Plexiglas and can be disposed in a common test probe housing.

Finally, the device according to an embodiment of the invention comprises a display unit, e.g. an LCD, connected to the control unit. The control unit is in that case configured to generate a graphic representation of the workpiece on the display unit.

BRIEF DESCRIPTION OF THE DRAWINGS

Other advantages and features are apparent from the dependent claims as well as from the following exemplary embodiments. The exemplary embodiments are to be understood not to be limiting; they serve for rendering the invention described above in a general manner comprehensible to the person skilled in the art. The exemplary embodiments will be explained with reference to the drawing. In the drawing:

FIG. 5: shows a C image recorded on the solid shaft section according to FIG. 3, and FIG. 6: shows a three-dimensional representation of the solid shaft section from FIG. 3 with detected flaws signals Fi drawn in.

DETAILED DESCRIPTION

Figure 1:
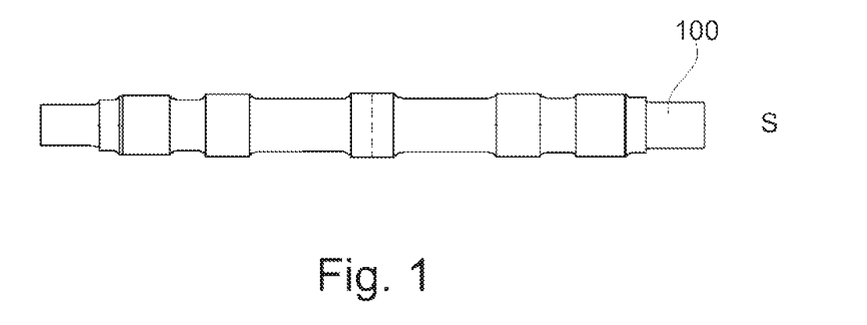
FIG. 1: shows a side view of a typical solid shaft of a wheel set of a rail vehicle.

FIG. 1 shows a side view of a typical solid shaft 1 of a wheel set of a rail vehicle. It is a rotationally symmetric forging with a diameter changing from section to section, as becomes clear from FIG. 1. In particular, the shaft 1 comprises different sections with a constant diameter, which are provided for accommodating the wheel hubs, the rolling bearings, with which the solid shaft is rotatably mounted on the rail vehicle, and a centrally disposed brake disk. As a forging, a solid shaft according to FIG. 1 typically has a certain anisotropy of the sound velocity for ultrasound, which is produced by local structural changes caused by the forging process. In this case, the solid shaft 1 is rotationally symmetric to the drawn-in axis of rotation S.

Figure 2:
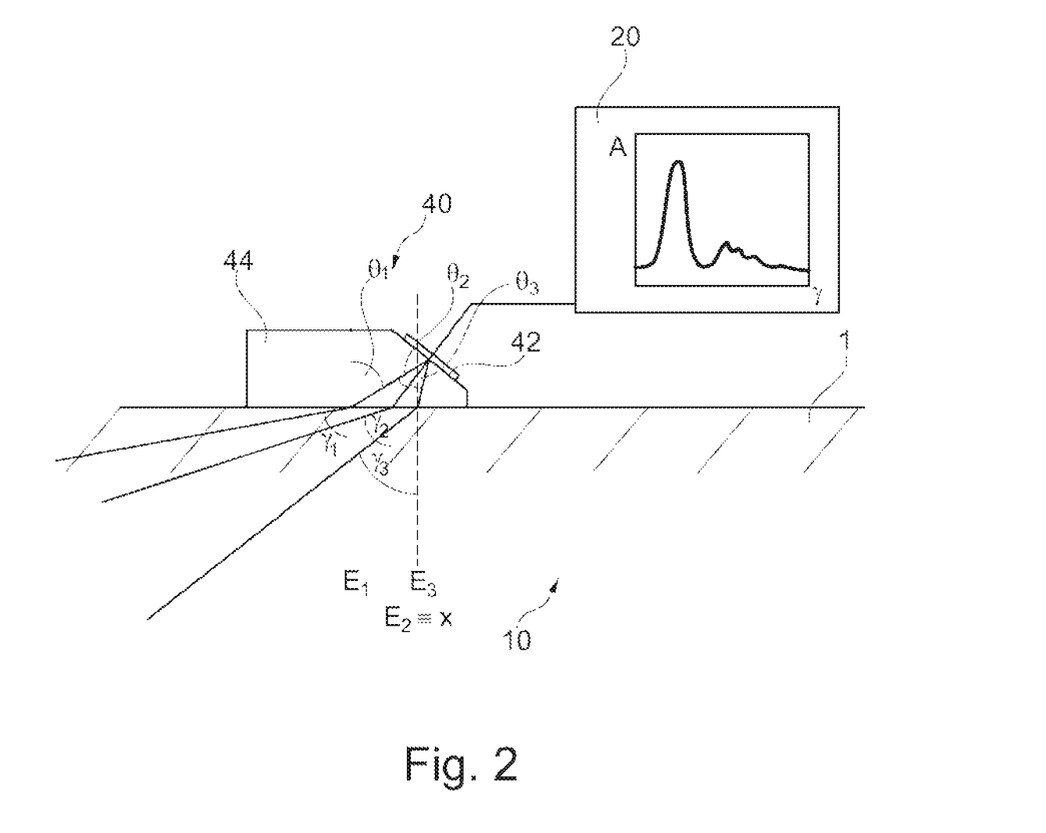
FIG. 2: shows a schematic representation of a test probe and a control unit according to a first exemplary embodiment of a testing device according to the invention.

FIG. 2 shows a first exemplary embodiment of a testing device 10 according to the invention, which comprises a control unit 20 and a test probe 40 connected to it. The test probe 40 comprises a segmented ultrasonic transducer 42 of the phased array type. It therefore comprises a plurality of individually controllable transducer elements (not shown). In this case, the segmented ultrasonic transducer 42 is disposed on a leading body 44 which in turn consists of a material suitable for oblique insonification into a forged steel workpiece. The leading body 44 often consists of polystyrene, polycarbonate or Plexiglas®. Generally, both the leading body 44 as well as the segmented transducer 42 are disposed in a common test probe housing (not shown) in order to shield them from environmental influences. In FIG. 2, the test probe 40 is shown placed on the cylindrical surface of a rotationally symmetric workpiece 1, which can be, for example, the solid shaft 100 shown in FIG. 1. The contact surface which is formed by the leading body 44 and with which the test probe is placed on the surface of the workpiece 1 therefore also has a hollow-cylindrical shape whose internal diameter is matched to the external diameter of the workpiece 1. As was already explained in the introduction, there are a lot of different shaft geometries that can also be completely curved in the longitudinal direction, i.e. it is possible that the workpiece to be inspected has no purely cylindrical region with a constant diameter. Using the technical teaching known from PCT/EP2010/056614, the use of test probes whose leading bodies are adapted to the cross section of the workpiece both in the longitudinal direction as well as the transverse direction is also possible. This adaptation is generally effected locally, i.e. for a predetermined X position relative to the axis of symmetry S of the workpiece.

The control unit 20 is configured for controlling the test probe 40 in such a way that it generates an ultrasonic test pulse that is coupled into the workpiece 1 at a defined insonification angle Theta. Furthermore, the control unit 20 is configured to adjust the insonification angle Theta in a controlled manner. By way of example, FIG. 2 shows three sound paths of three ultrasonic test pulses coupled into the workpiece 1 at different insonification angles Theta 1, Theta 2 and Theta 3. While the insonification angles Theta 1, Theta 2 and Theta 3 can be controlled with very good accuracy by the control unit 20, the entrance angles Gamma 1, Gamma 2 and Gamma 3 resulting in the workpiece 1 are associated with a certain uncertainty that is directly linked to the above-mentioned anisotropy of the sound velocity for ultrasound in the forged solid shaft 100. It is also immediately apparent from FIG. 2 that, given a constant test probe position X, the coupling location E changes slightly if the insonification angle Theta is varied, due to the refraction during the transition into the workpiece, i.e. given a constant position X, a different coupling location E 1, 2, 3 is obtained for each insonification angle Theta 1, 2, 3. If the requirements with respect to the accuracy of the inspection are not too high, this effect can be neglected, e.g. in determining the position w at which the sound path W hits the internal workpiece surface for a given insonification angle Theta and a given test probe position X. In the case of higher requirements with regard to accuracy, it can be taken into account by calculation, e.g. when determining the position w.

Furthermore, the control unit 20 is configured to record, by means of the test probe 40, an ultrasonic echo signal in a time-resolved manner from the workpiece 1, and, in an embodiment, at the angle Theta, and to then digitize it in a selected travel time interval I. In this connection, the control unit 20 is configured to select a travel time interval I depending on the sound path W of the ultrasonic test pulse in the workpiece 1, with this selected travel time interval corresponding to a near-surface region of the workpiece 1. As was already mentioned in the introduction, the sound path of the ultrasonic test pulse in the workpiece is generally dependent on the workpiece geometry, the test probe position X as well as on the insonification angle Theta and the inclination angle Phi (which was defined in the introductory part and is, in an embodiment, zero) and on the acoustic properties of the workpiece. In particular, the control unit 20 can be configured to permit the user to autonomously define the above-mentioned near-surface region depending on the workpiece geometry. In this case, the specifically selected test probe position can also be taken into account.

In an embodiment, the ROI is defined via the travel time interval I selected (and thus to be analyzed) for a given insonification angle Theta. The basis is the sound velocity for the ultrasonic test pulse in the workpiece, which can be specified only with a certain uncertainty. The start of the travel time interval I is defined by the time 2tROI EIN at which the ultrasonic test pulse hits the internal surface for the first time at the earliest, i.e. the highest possible sound velocity is generally used as a basis. The end of the travel time interval I is defined by the time 2tROI AUS at which the ultrasonic test pulse hits the internal surface for the first time at the latest, i.e. the lowest possible sound velocity is generally used as a basis. In individual cases, deviations may result due to the workpiece geometry and the change of travel paths W due to the change of the entrance angle Gamma (cf. FIG. 2) in the case of a variation of the sound velocity. It is thus ensured that the ultrasonic test pulse hits the internal workpiece surface in the selected travel time interval I with certainty, i.e. the internal surface lies within the ROI in every case.

Optionally, the travel time interval I to be analyzed, and thus the ROI, can be additionally enlarged by a defined "allowance" (e.g. ±5%, ±10%, ±15%) added to the maximum or minimum sound velocity to be presumed. This constitutes an advantageous development of the above-mentioned embodiment. It can thus be accomplished that a near-surface region with a defined, in particular constant, thickness of, for example, 30 to 60 mm, or 40 mm and above, is always being examined.

As mentioned above, the control unit 20 is configured to select a "near-surface" travel time interval I. Then, the control unit 20 digitizes and analyzes the recorded ultrasonic echo signals in the selected "near-surface" travel time interval I with regard to flaw signals Fi, i.e. with regard to ultrasonic echo signals that indicate near-surface flaws in the workpiece 1, such as incipient cracks or near surface defects. In the simplest case, only a maximum echo amplitude in the travel time interval I is determined here, and no assessment of the echo amplitude as a "flaw signal Fi" or "no flaw signal" is made. Rather, the echo amplitude (or a similar value obtained in a more discriminate manner) itself is considered as a flaw signal Fi, i.e. there is at least one flaw value Fi for each test probe position X, each insonification angle Theta and each rotation angle beta (see below).

Figure 3:
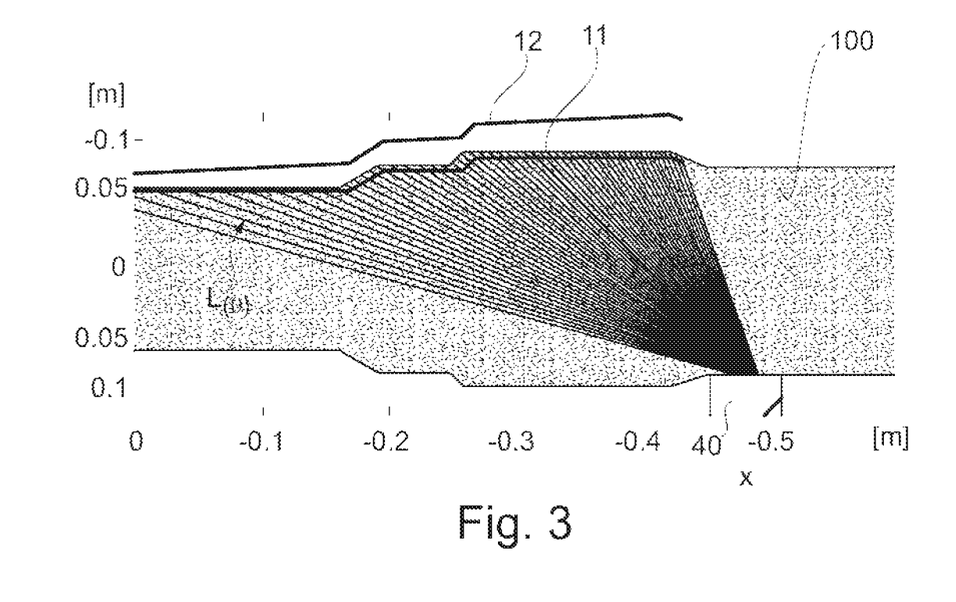
FIG. 3: shows a partial sectional representation through the solid shaft from FIG. 1 for illustrating the sound paths of the ultrasonic test pulses in the workpiece and the ROI.

The concept according to the invention of the selection of a near-surface region, the region of interest, is illustrated by means of FIG. 3, which presents a partial sectional representation of the solid shaft 100 from FIG. 1. FIG. 3 shows the sound paths W of a plurality of ultrasonic test pulses that are coupled into the workpiece 1 at a substantially constant coupling location E by means of the stationary test probe 40 disposed at the position X on the surface of the workpiece 1. In the process, the insonification angle Theta is successively varied, from one ultrasonic test pulse to the next, between preset limits, which are typically between 20 and 75°. In this way, an extensive section of the internal surface of the solid shaft 100 opposite from the test probe position X or the coupling location E is scanned by the ultrasonic test pulses. For each ultrasonic test pulse insonified into the solid shaft 100 at a certain insonification angle Theta, the test probe 40 acquires in a time-resolved manner the echo signal returning from out of the solid shaft 100 at the angle Theta. If the ROI has been previously defined depending on the geometry of the workpiece 1 to be inspected, as this is indicated in FIG. 3 by the lines 11 and 12, then, given a known coupling location, it is possible for every insonification angle Theta set by the control unit 20 to determine the travel time tROI_EIN until the ultrasonic test pulse insonified into the workpiece 1 at the angle Theta reaches the ROI. Due to the sound velocity in the material of the workpiece 1, which is known per se, this travel time tROI_EIN corresponds to a travel distance $L_{ROI\_EIN}$ in the workpiece, as becomes clear from FIG. 4.

Figure 4:
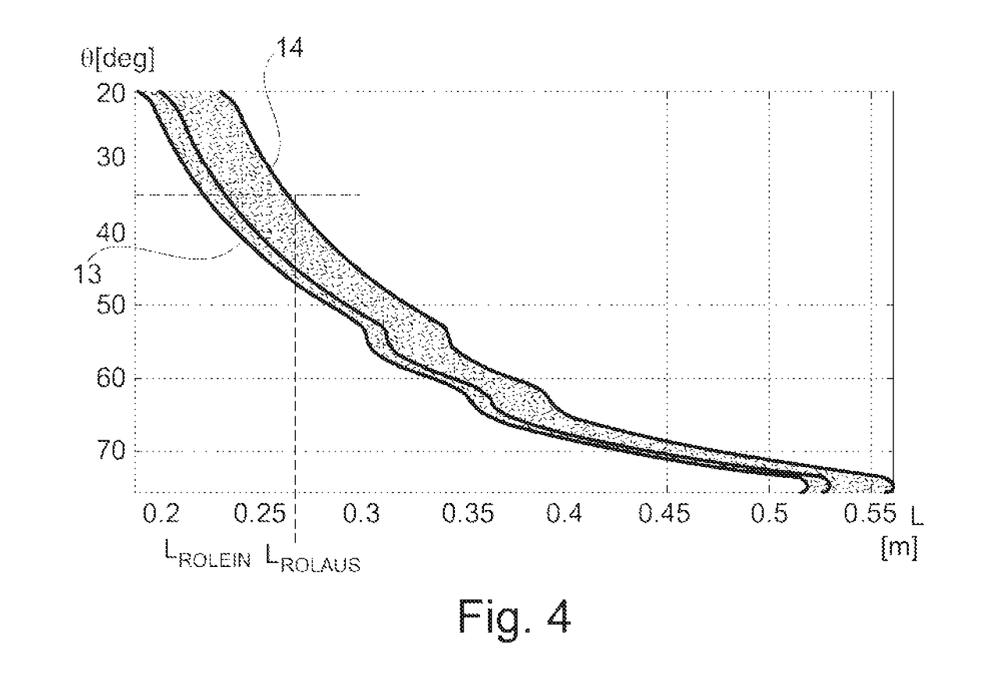
FIG. 4: shows a diagram from which the data reduction due to the introduction of the ROI becomes apparent.

FIG. 4 now shows, for the ROI defined in FIG. 3 by the lines 11 and 12, the value range I of the response time, or the travel distance L, in the solid shaft 100 which has to be analyzed, at a given insonification angle Theta, with regard to relevant flaw signals in order to detect such flaws that are situated in the ROI. By way of example, travel distances $L_{ROI\_EIN}$ (=entrance ROI) as well as $L_{ROI\_AUS}$ (=exit ROI) are drawn in for an insonification angle Theta=35°.

Here, it is possible, at a given test probe position X, for any insonification angle Theta, to record the echo signal in a time-resolved manner for a predetermined duration I after coupling in the ultrasonic test pulse. In this case, the duration I is selected in such a way that, for the selected range of the insonification angle Theta, for the selected test probe position X, as well as for the geometry and the material properties of the workpiece, it is ensured that echo signals from the ROI 10 are always still acquired with regard to time. This means that a digitized echo signal exists for each point within the ROI shown in the diagram according to FIG. 4, which is situated between the lines 13 and 14. According to the invention, only those echo signals from the ROI are examined for flaw signals Fi. Thus, the echo signals to be evaluated are limited by the selection of echo signals that originate from the ROI. Therefore, the lines 11 and 12 from FIG. 3 are in this case translated, based on the physical laws, into the lines 13 and 14 in FIG. 4. The set of those measurement points that lie within these two boundary lines in FIG. 4 then forms a subset of the data points to be analyzed, which is selected according to the invention. This is obtained in accordance with the approach of the present invention by the echo signal, which is provided for a long travel time interval, being digitized and analyzed only within a small window in time I.

Thus, the insight resulting from FIG. 4 is utilized already during the execution of the ultrasound inspection. For a workpiece with known material properties and a known geometry, an ROI is defined analogously to the representation in FIG. 3. For a given test probe position, the relationship between the insonification angle Theta and the response time or travel distance in the workpiece, which is apparent from FIG. 4, is exploited in order to determine, for every insonification angle Theta, the response time interval I in which signals are to be expected that are to be ascribed to flaws in the ROI. For a given test probe position X, the ultrasonic inspection is then limited to the above-mentioned response time interval I for each individual electronically set insonification angle Theta.

Within the context of the method according to the invention, those echo signals that can be traced back to the ROI are subsequently analyzed with respect to flaw signals by the correspondingly configured evaluation unit 20. For example, such a flaw analysis can be based on the amplitude of echo signals, wherein, in this case, use can be made of all of the methods for signal evaluation and, optionally, signal improvement, e.g. for increasing the signal-to-noise ratio, as was already mentioned in the general part.

Within the context of the exemplary embodiment an echo value G is determined during the flaw analysis, which is then assigned to a point w on the surface of workpiece 1, e.g. the location of the first incidence of the ultrasonic test pulse on the internal surface of the workpiece 1. In this case, the uncertainty with regard to the entrance angel Gamma resulting from the uncertainty with respect to the local sound velocity, and the uncertainty with regard to the location of the first incidence on the internal surface of the workpiece 1 resulting therefrom, is, in an embodiment, neglected. This echo value G is determined by determining the echo value with the highest amplitude in the selected travel time interval I. This maximum amplitude value is then assigned to the above-mentioned point (location of first incidence) on the surface of the workpiece 1.

Figure 6:
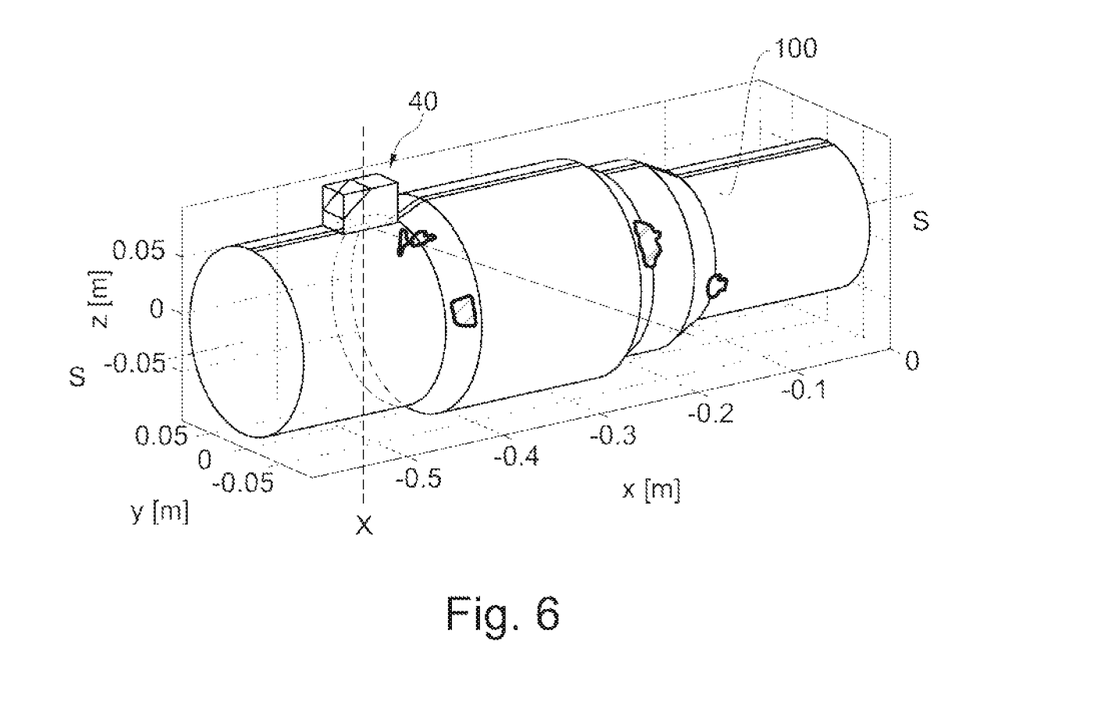

FIG. 6 illustrates the actual conditions in an inspection task on a rotationally symmetric workpiece 1. In this case, FIG. 6 is a three-dimensional representation 50 generated according to the invention of the shaft section of the solid shaft 100 from FIG. 1 apparent from FIG. 3. A guiding device (not shown) is provided with which the test probe 40 is retained on the surface of the solid shaft 100 while maintaining the position X (X position in FIG. 6) relative to the axis of symmetry S and the orientation of the test probe 40 (characterized by the inclination angle Phi relative to the insonification plane P).

While the inspection method is carried out, the solid shaft 100 is rotated, by means of a rotating device which is not shown, by 360° or an integral multiple thereof about its axis of symmetry S, which coincides in FIG. 6 with the X axis. The rotation angle of the solid shaft about its axis of symmetry is in this case referred to as Beta; it is acquired by means of a suitable angle encoder (not shown). At a fixed X position of the test probe 40, the entire range of the insonification angle Theta accessible by means of the test probe 40 is electronically tuned for every rotation angle Beta by means of the control unit 20. For each individual insonification angle Theta, the echo signal is recorded in a time resolved manner and digitized in the selected travel time interval I (Theta). The data points thus obtained can be plotted in a diagram according to FIG. 4. That is, from the entirety of the recorded echo signals, those are being selected, with regard to time, that correspond to the selected ROI. These echo signals are then digitized, i.e. a set of data points to be analyzed are generated for a given insonification angle Theta.

Figure 5:
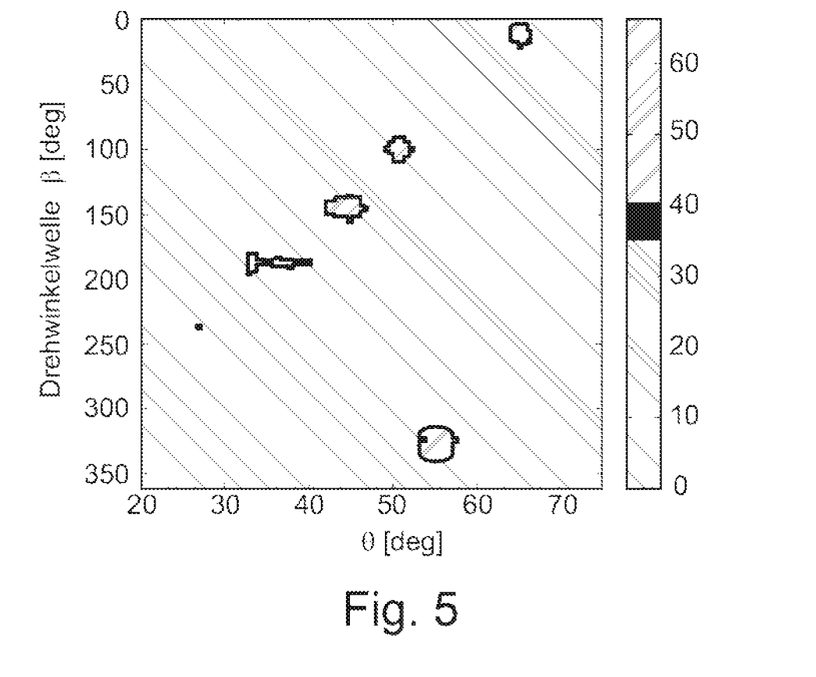

To each individual point w on the surface of the solid shaft 100, an echo value G (w) is assigned which corresponds to the maximum signal from the ROI as-signed to this point. If this method is carried out for a plurality of rotation angles Beta, which can, for example, be gone through gradually in steps of 0.5 to 1° up to a total rotation angle Beta of at least 360°, then it is possible to plot the signal values obtained into a so-called C image. In such a C image, the signal value assigned to an echo signal is plotted into a diagram according to FIG. 5, in which, for example, the insonification angle Theta is used as the abscissa and the rotation angle Beta of the solid shaft 100 as the ordinate. In this case, the echo value G can be coded, for example, by means of brightness values or in color. A three-stage scale was used in FIG. 5. If an echo value G remains below a registration limit, then this point is marked brightly in the C image according to FIG. 5. If it exceeds a registration limit but does not yet have to be assigned to a flaw size that is considered critical, then it is coded with a second (e.g. darker, e.g. orange) color value. Finally, if the echo value G exceeds a value that is assigned to a critical flaw size, it is coded with a third color value, e.g. in the signal color red. A diagram according to FIG. 5, which results in this way, already has a high informative value for an expert user of a device according to the invention.

The interpretability of the result according to FIG. 5 is improved yet again if it is not the insonification angle Theta that is used as the abscissa, but the X position (position relative to the axis of symmetry S of the workpiece) of the point w on the workpiece surface assigned to the ROI. The representation that results in this manner substantially corresponds to the representation according to FIG. 5, but is suitable for a direct transfer onto the three-dimensional representation of the examined solid shaft 100 of FIG. 6 generated according to the invention. The color-coded signal values are then plotted on the surface of the three-dimensionally represented workpiece depending on the rotation angle Beta of the shaft 100 and on the position on the axis of symmetry of the shaft 100 (position on the X axis). The result is the flaw representation apparent from FIG. 6, which has an enormously improved interpretability over the visualization methods known so far from the prior art.

Particular advantages also result, in particular, when the representation according to FIG. 6 is designed in such a way that a rotation of the shaft 100 about its axis of symmetry S can be shown. This is possible, for example, in a CAD model of the solid shaft 100 with the echo values G (w) plotted in a spatially resolved manner on its surface. A moving representation of the rotation of the solid 10 shaft 100 about the rotation angle Beta as a sequence of individual images that combine into a film is also conceivable, and protection is sought therefor.

What is claimed:

1. A method comprising:
   insonifying a plurality of ultrasonic test pulses into a rotationally symmetric workpiece at a surface coupling location via a phased array test probe coupled to the workpiece, wherein each of the plurality of ultrasonic test pulses is obliquely insonified into the workpiece at a defined insonification angle which differs between each respective ultrasonic test pulse of the plurality of ultrasonic test pulses;
   recording a plurality of ultrasonic echo signals received from the workpiece, each of the plurality of ultrasonic echo signals respectively corresponding to each of the plurality of ultrasonic test pulses insonified via the phased array test probe;
   selecting a travel time interval associated with a sound path of each of the plurality of ultrasonic test pulses, wherein a start of the travel time interval being defined based on a first sound velocity for the plurality of ultrasonic test pulses in the workpiece and an end of the travel time interval being defined based on a second sound velocity for the plurality of ultrasonic test pulses in the workpiece, the selected travel time interval corresponding to a near-surface region of the workpiece and defining a region of interest;
   generating an echo value for each of the plurality of ultrasonic echo signals by analyzing the plurality of ultrasonic echo signals in the selected travel time interval, wherein a largest amplitude of the ultrasonic test pulse occurring in the selected travel time interval is used as the echo value; and
   generating a representation of the near-surface region of the workpiece, wherein the echo value is depicted in the representation.

2. The method according to claim 1, wherein the representation of the near-surface region of the workpiece is two-dimensional or three-dimensional.

3. The method according to claim 1, wherein a point at which an echo value is depicted in the representation of the workpiece is assigned to a sound path of an ultrasonic test pulse in the workpiece.

4. The method according to claim 1, wherein the plurality of ultrasonic echo signals in the selected travel time interval are subjected a travel time-dependent and/or an insonification angle-dependent amplification.

5. The method according to claim 1, further comprising repeating insonifying, recording, generating an echo value, and generating a representation in one or more fixed surface coupling locations.

6. The method according to claim 5, wherein a mean value of the generated echo values is determined and presented in a spatially resolved manner in the representation.

7. The method according to claim 1, wherein the travel time interval is selected in such a way that the ultrasonic test pulse reaches the near-surface region of the workpiece within the travel time interval.

8. The method according to claim 1, wherein the plurality of ultrasonic test pulses are insonified into the workpiece via placement of the phased array test probe at a plurality of surface coupling locations relative to an axis of symmetry of the workpiece, the ultrasonic test pulses insonified into the workpiece at different insonification angles and further wherein steps of insonifying, recording, selecting, generating an echo value, and generating a representation are carried out for each of the plurality of ultrasonic test pulses.

9. The method according to claim 1, wherein the sound path of the insonified ultrasonic test pulses and an axis of symmetry of the rotationally symmetric workpiece share a common insonification plane.

10. The method according to claim 9, wherein the plurality of ultrasonic test pulses are insonified into the workpiece such that the common insonification plane rotates about the axis of symmetry of the rotationally symmetric workpiece.

11. The method according to claim 10, wherein the common insonification plane is rotated by an integral multiple of 360°.

12. The method according to claim 1, wherein the plurality of ultrasonic test pulses are insonified into the workpiece such that a travel direction of a first part of the ultrasonic test pulses has a first component in the same direction as an axis of symmetry of the workpiece, and the travel direction of a second part of the ultrasonic test pulses has a second component oriented contrary to the direction of the axis of symmetry of the workpiece.

13. The method according to claim 1, wherein the workpiece has an anisotropic sound velocity for ultrasound.

14. The method according to claim 1, wherein the workpiece is a forged solid shaft.

15. A device comprising:
   a phased array test probe for insonifying a plurality of ultrasonic test pulses into a rotationally symmetric workpiece having a diameter that changes from section to section and for recording a plurality of ultrasonic echo signals from the workpiece, wherein each ultrasonic test pulse of the plurality of ultrasonic test pulses is obliquely insonified into the workpiece at a defined insonification angle which differs between each respective ultrasonic test pulse of the plurality of ultrasonic test pulses; and
   a control unit, operatively coupled to the phased array test probe and configured to
   control the phased array test probe to insonify the plurality of ultrasonic test pulses into the workpiece at the defined insonification angle,
   record a plurality of ultrasonic echo signals from the workpiece,
   select a travel time interval depending on a sound path of the plurality of ultrasonic test pulses in the workpiece, a start time interval being defined based on a first sound velocity for the plurality of ultrasonic test pulses in the workpiece, and an end of travel time interval being defined based on a second sound velocity for the plurality of ultrasonic test pulses in the workpiece, the selected travel time interval corresponding to a near-surface region of the workpiece and defining a region of interest,
   generate an echo value based on analyzing the plurality of recorded ultrasonic echo signals in the selected travel time interval, wherein a largest amplitude of one of the plurality of ultrasonic echo signals occurring in the selected travel time interface is used as the echo value, and
   generate a representation of a near-surface region of the workpiece, wherein the echo value is depicted in the representation.

16. The device according to claim 15, wherein the plurality of ultrasonic test pulses reach the near-surface region of the workpiece within the selected travel time interval.

17. The device according to claim 15, further comprising a guiding device configured to orient the phased array test probe relative to an axis of symmetry of the workpiece such that a sound path of the insonified ultrasonic test pulses and the axis of symmetry of the workpiece span a common insonification plane.

18. The device according to claim 15, wherein the phased array test probe comprises a plurality of ultrasonic transducers divided into a plurality of individually controllable transducer segments, and the control unit is further configured to cause the transducer segments to insonify the workpiece at different insonification angles via the plurality of ultrasonic test pulses.

19. The device according to claim 15, further comprising a rotating device configured to cause the workpiece to be rotated about an axis of symmetry relative to a position of the phased array test probe.

20. The device according to claim 15, wherein the phased array test probe comprises a first ultrasonic transducer and a second ultrasonic transducer, and a first travel direction of a first plurality of ultrasonic test pulses insonified into the workpiece via the first ultrasonic transducer relative to an axis of symmetry of the workpiece is oriented contrary to a second travel direction of a second plurality of ultrasonic test pulses insonified by the second ultrasonic transducer into the workpiece.

21. The method of claim 1, wherein the first sound velocity is a highest possible sound velocity and the second sound velocity is a lowest possible sound velocity.

22. The device of claim 15, wherein the first sound velocity is a highest possible sound velocity and the second sound velocity is a lowest possible sound velocity.

* * * * *